United States Patent

Clarke

[19]

[11] Patent Number: 5,855,215
[45] Date of Patent: Jan. 5, 1999

[54] TOOTHPICKS AND TOOTHPICK FRAME

[76] Inventor: Royce Steven Clarke, 6 Lewin Road, Epsom, Auckland, New Zealand

[21] Appl. No.: 51,281
[22] PCT Filed: Oct. 10, 1996
[86] PCT No.: PCT/NZ96/00114
   § 371 Date: Apr. 7, 1998
   § 102(e) Date: Apr. 7, 1998
[87] PCT Pub. No.: WO97/13472
   PCT Pub. Date: Apr. 17, 1997

[30] Foreign Application Priority Data

Oct. 12, 1995 [NZ] New Zealand .......................... 280215

[51] Int. Cl.$^6$ ................................................ A61C 15/00
[52] U.S. Cl. ........................................ 132/321; 132/329
[58] Field of Search .................................. 132/321, 328, 132/329; 206/63.5, 368, 369, 370, 553, 820; 433/141, 142, 143, 372

[56] References Cited

U.S. PATENT DOCUMENTS

| | | | |
|---|---|---|---|
| 2,477,194 | 7/1949 | Millard | 132/329 |
| 2,762,501 | 9/1956 | Cameron | 132/329 |
| 3,136,416 | 6/1964 | Goldrosen | 206/372 |
| 3,438,486 | 4/1969 | Pinkas | 132/321 |
| 4,040,433 | 8/1977 | Edison | 132/321 |
| 5,234,009 | 8/1993 | Lemon et al. | 132/321 |

FOREIGN PATENT DOCUMENTS

| | | | |
|---|---|---|---|
| 1101693 | 3/1961 | Germany | 132/329 |
| 2737457 | 2/1979 | Germany | 132/329 |

*Primary Examiner*—Todd E. Manahan
*Attorney, Agent, or Firm*—Kenyon & Kenyon

[57] ABSTRACT

This invention relates to a toothpick holder and toothpicks. The toothpicks are provided in and securely attached by at least one part to a support means which provides protection on at least one end and both sides of the toothpick or toothpicks in one plane. The toothpick or toothpicks are therefore protected from damage by unintentional forces applied in those planes. The toothpick holder will generally incorporate a plurality of toothpicks, and may also include a holding means for used toothpicks and a base plate for securing the holder in a match-book-type folder. The invention also relates to particular designs of toothpicks held in the support means, said toothpicks having a substantially square or rectangular handle end and a scalpel-shaped blade end, upper and side edges of which come to a point to form the pick end.

12 Claims, 5 Drawing Sheets

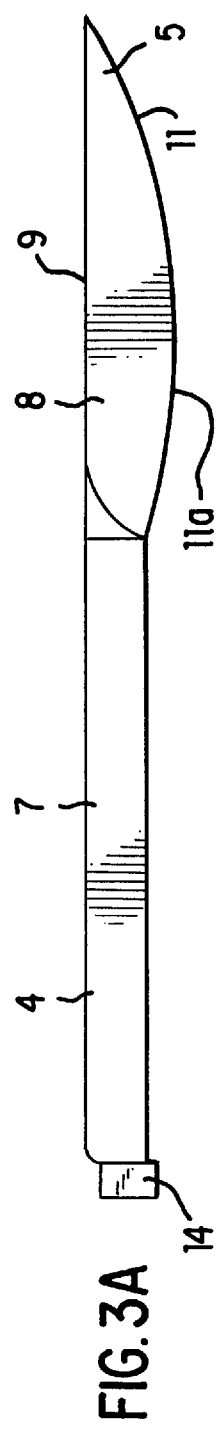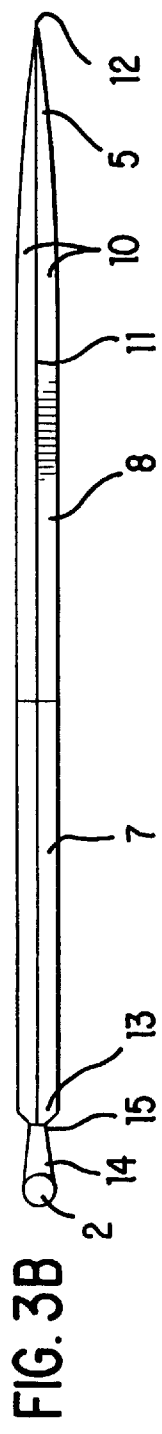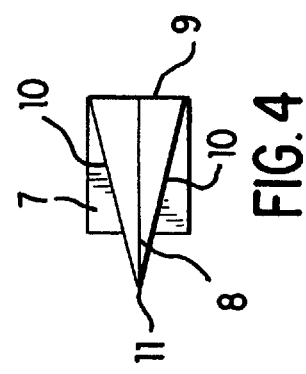

TOOTHPICKS AND TOOTHPICK FRAME

BACKGROUND TO THE INVENTION

Toothpicks are generally provided as single items, or in containers holding a plurality of separate toothpicks. They may be of wood or synthetic plastics. It is not generally practical for an individual to carry single toothpicks in their pockets, purse, handbag, etc. The toothpicks are easily lost, readily broken, and it is not very hygienic. Furthermore, the containers for holding a plurality of toothpicks are not generally designed for personal use, but rather for offering toothpicks for use in public places, such as restaurants.

It is important that toothpicks, and especially the pick end or ends, be protected from damage. Further, where a plurality of picks are provided in a container or holder it is important that each pick be securely retained and protected in the container or holder until it is required.

Thus, it is an object of the present invention to provide toothpicks in a toothpick holder which provides a convenient personal package and which protects the toothpicks from damage, and/or which reduces or overcomes some of the above mentioned problems, or at least which provides the public with a useful alternative.

Other objects of the invention will become apparent from the following description which is given by way of example only.

DISCLOSURE OF INVENTION

According to one aspect of the present invention there is provided a toothpick holder comprising a peripheral frame defining a space in which a plurality of toothpicks are confined, each toothpick comprising a handle and a blade and formed integrally with but separable from said peripheral frame at an end of the handle remote from the blade, and said peripheral frame providing protection for the toothpicks from forces applied in at least two orthogonal directions.

In a preferred form of the invention adjacent toothpicks may be oppositely disposed in the peripheral frame, the handle ends of adjacent toothpicks connected to opposite sides of the frame.

In a further preferred form of the toothpick holder of the present invention, the peripheral frame may have a base plate adapted to attach the toothpick holder in a match-book-type folder.

In a further preferred form, the toothpick holder may further comprise at least one holding means for retaining a used toothpick.

Preferably said holding means may comprise a receiving means on the peripheral frame, said receiving means adapted to receive the handle end of a toothpick and hold said toothpick securely in the peripheral frame.

Preferably the handle of each toothpick may have a polygonal cross-section, most preferably square.

In a preferred form of the invention said blade of each toothpick may have a triangular cross-section with an upper edge and angled sides forming a sharpened lower edge, said upper edge forming a point at one end, opposite the handle end, and said sharpened lower edge curving to meet said point of said upper edge to form the pick end of the toothpick.

Preferably, an angle between the sides of the blade at the sharpened lower edge may be between substantially 25° and 30°, and most preferably substantially 27°.

In one preferred form of the invention the toothpick holder may be made of plastics material, and preferably manufactured as a single piece by injection moulding.

Other aspects of the present invention may become apparent from the following description which is given by way of example only, and with reference to the accompanying drawings.

BRIEF DESCRIPTION OF DRAWINGS

FIG. 3 Shows A. a side view and B. a plan view of one embodiment of a toothpick of a toothpick holder of the present invention.

FIG. 4 Shows a front end view of the toothpick of FIG. 3.

DETAILS DESCRIPTION OF THE INVENTION

Figure 1:
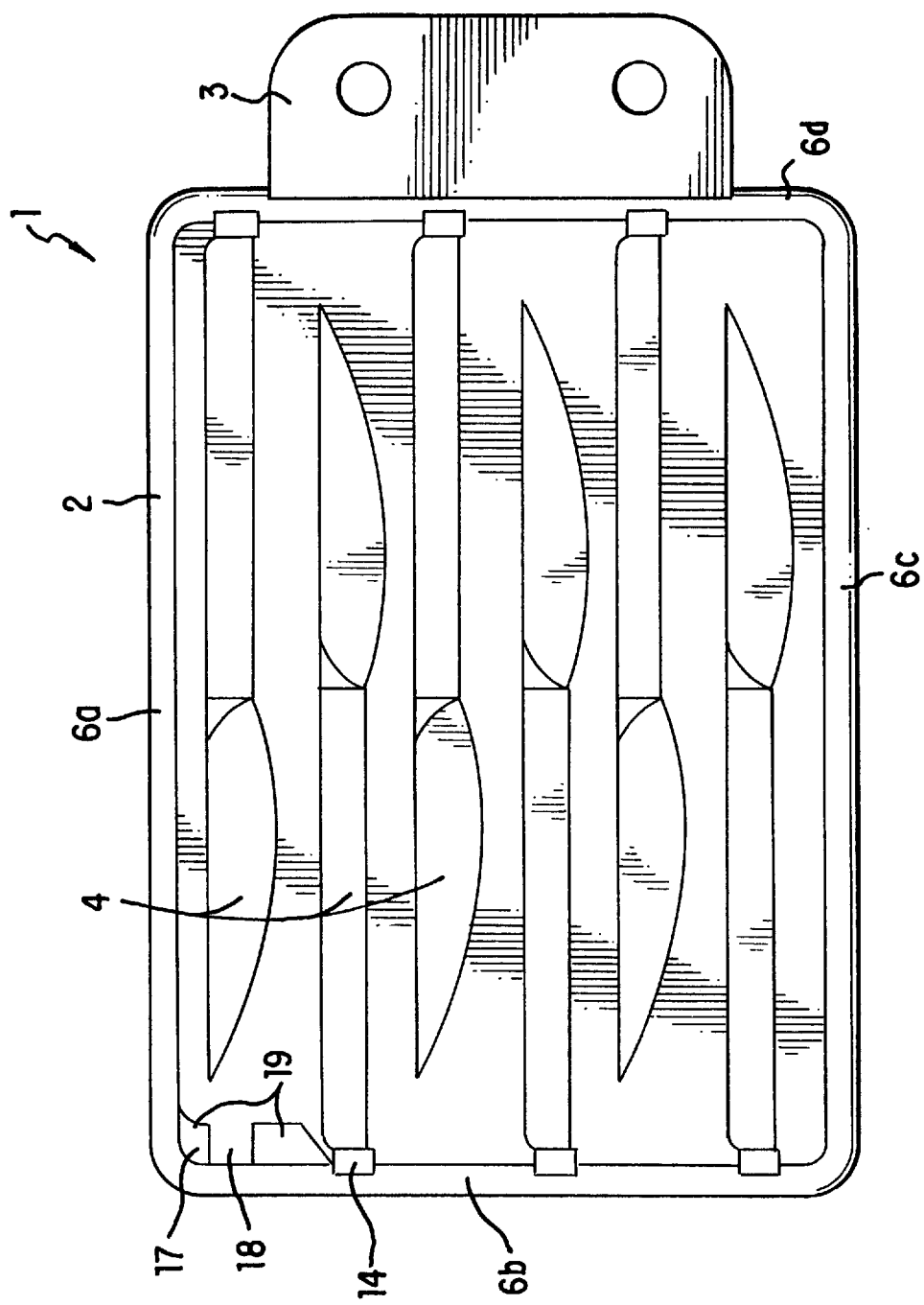
FIG. 1 Shows a plan view of a toothpick holder of the present invention in one embodiment.

A toothpick holder 1 of the present invention, in a preferred embodiment, as shown in FIG. 1, may comprise support means 2, base plate 3 and a plurality of toothpicks 4.

Figure 2:
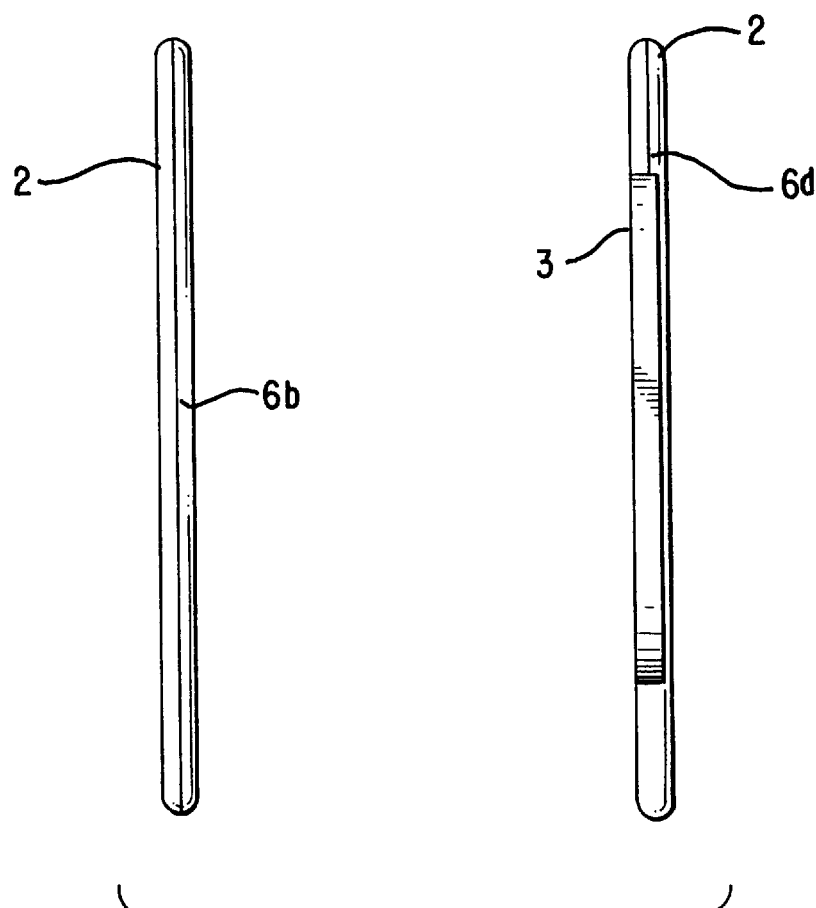
FIG. 2 Shows views from each end of the toothpick holder of FIG. 1.

In the embodiment shown in FIGS. 1 to 3 the support means 2 is a frame, substantially square or rectangular in shape. In this embodiment the support means 2 entirely surrounds the plurality of toothpicks 4 in one plane. Thus, pressure applied transverse to that plane, in the form of an unintentional force, would not cause individual toothpicks to bend and be dislodged from the support means 2. Intentional force applied within the frame to a single toothpick would however, be able to separate a toothpick for use. Further, the toothpicks 4, and especially the pointed or pick ends 5, are protected from damage by forces applied parallel to the plane of the support means 2, i.e. the plurality of toothpicks 4 are situated within the plane of the support means and protected by its sides 6a, b, c, d.

Each toothpick 4 has a handle 7 and a blade 8. Referring to FIGS. 3 and 4 it can be seen that, in a preferred embodiment, the handle 7 has a four-sided cross-section. The handle may alternatively have a circular or other polygonal cross-section. The blade 8 has a substantially triangular cross-section with a flat upper edge 9 and lateral sides 10 which form a lower knife edge 11. The upper edge 9 forms a point 1 2 opposite the handle end. The lower knife edge 11 has a curved profile which from an apex 11a curves to join the upper edge 9 at its point 12 to form the pick end 5 of the toothpick 4.

The angle at which the lateral sides 10 form the lower knife edge 11 is preferably in the range 25°–30° and, in the embodiment of the invention shown in the figures, is substantially 27°.

Each toothpick 4 may be connected to the support means 2 at the end 13 of its handle 7 by a connection member 14, this connection member 14 having a narrowed or weakened portion 15 which enables the toothpick 4 to be separated from the support means 2 by bending the toothpick 4 out of the plane of the support means.

In the embodiment shown in FIG. 1 adjacent toothpicks are oppositely disposed, and therefore connected to the support means 2 on opposite sides 6b, 6d. It will be appreciated that other configurations of toothpicks within the support means 2 are envisaged and included within the scope of this invention. For example, the toothpicks may all point in the same direction with the handles all connected on the same side of the support means, as shown in FIG. 5.

It will also be appreciated that a square or rectangular shape of support means 2 is only one example of the shape of support means 2 envisaged. Other shapes are envisaged although less practical.

Figure 5:
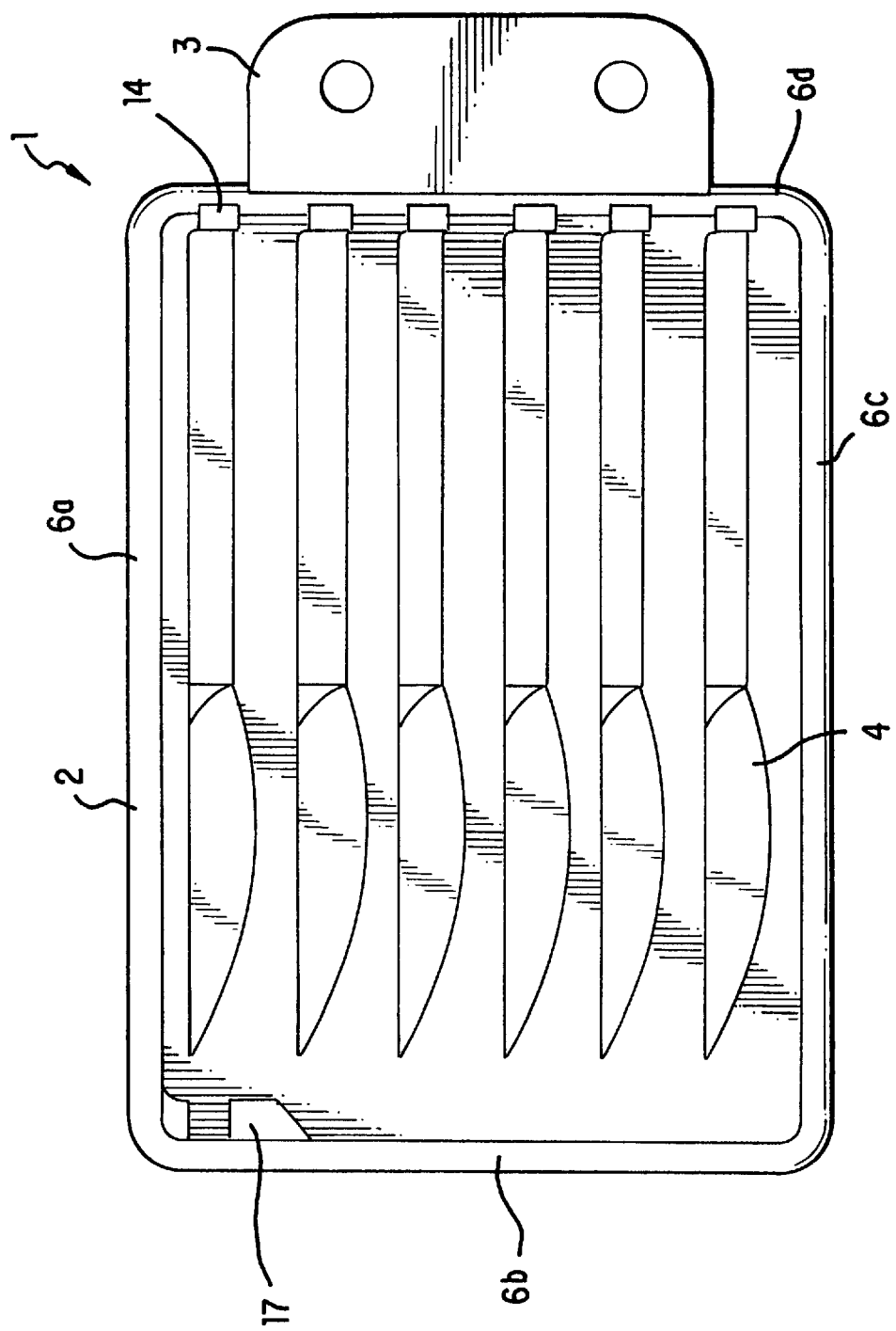
FIG. 5 Shows a plan view of a toothpick holder of the present invention in an alternative embodiment.

In addition, in the embodiment shown in FIG. 5, for example, in which the toothpicks 4 are all connected to the same side 6d of the support means 2, the support means 2 may only have three sides, comprising a base side 6d and two lateral sides 6a, b. With such a configuration the support means 2 would still provide protection against forces applied transverse to the plane of the support means, although less efficiently, as well as to forces applied parallel to the plane of the support means except at the open side.

Referring to FIG. 1 the support means 2 may also include a used toothpick receptacle 17. This receptacle 17 may comprise a slot 18 in a preformed part 19 of the support means 2. This slot 18 may have a cross-section corresponding with that of the end 13 of handle 7 of a toothpick 4, and is therefore adapted to receive the handle end 13 and hold it securely. Thus, once a toothpick 4 has been removed from the support means 2 for use, it may be returned to the support means for re-use. There may be a plurality of used toothpick receptacles 17 on the support means 2. However, it will be appreciated that in most cases a single receptacle will be sufficient since the product is intended to be a personalised toothpick holder and it is envisaged that only a single toothpick would be in use at any one time.

The toothpick holder 1 of the present invention may be of plastics material, and the preferred form of manufacturing is by injection moulding. It will be appreciated however that toothpick holders and toothpicks of the invention may be made of any substantially rigid material.

Figure 6:
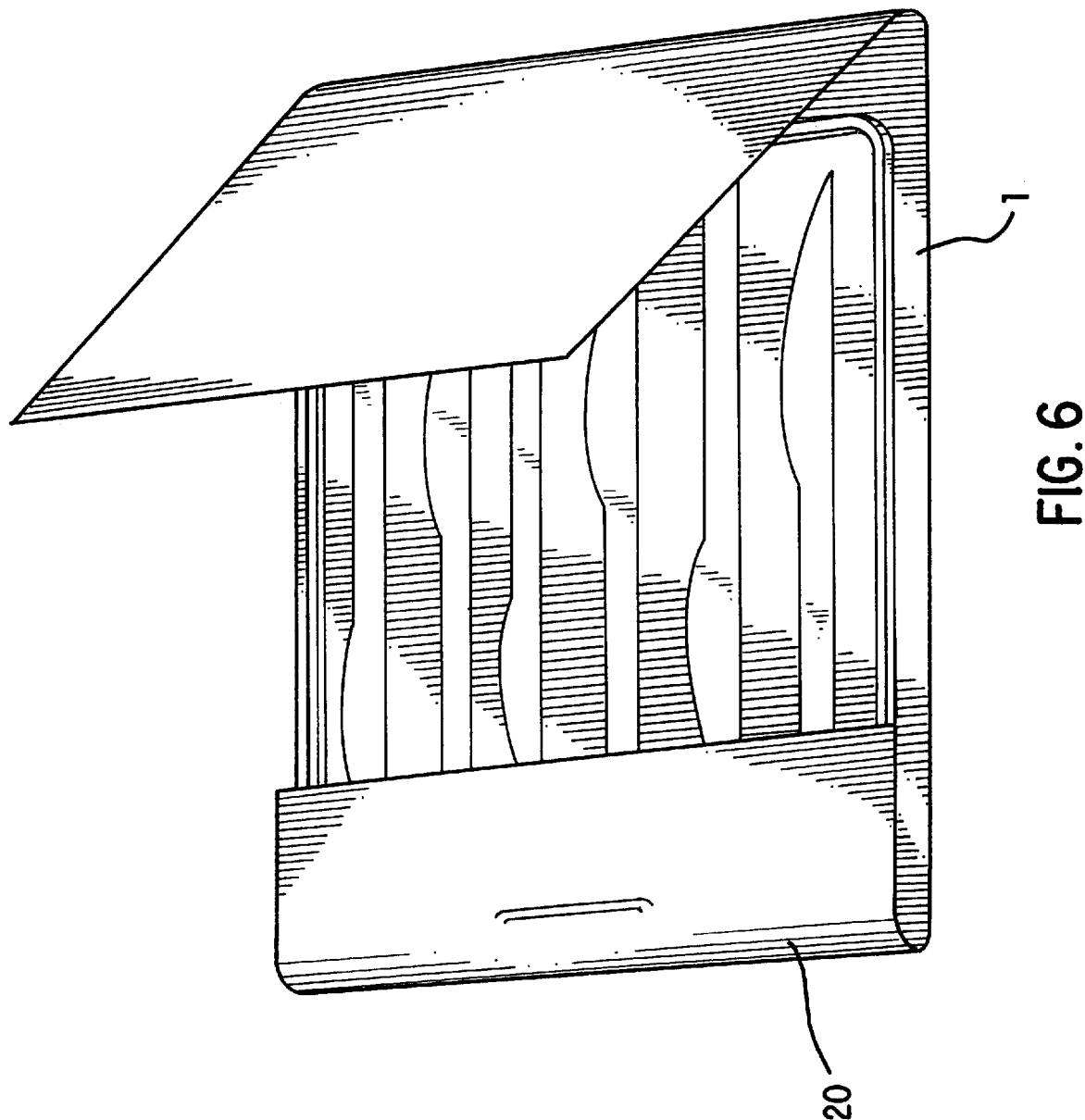
FIG. 6 Shows a toothpick holder of the present invention in a match-book-type folder.

The base plate 3 may be provided on a toothpick holder 1 of the present invention to enable the holder 1 to be incorporated into a match-book-type folder 20. With reference to FIGS. 1 and 5, the base plate 3 may be integrally formed with and extend from the support means 2, and may include holes for stapling in a match-book-type folder, as shown in FIG. 6. In this configuration advertising material can be applied to the folder 20, if required. Alternatively, it is envisaged that advertising material may be applied directly to the base plate 3.

It is also envisaged that toothpick holders 1 of the present invention may be packaged in sachet-type packages, such packaging again providing a source of advertising space.

Where in the foregoing description reference has been made to specific components or integers of the invention having known equivalents then such equivalents are herein incorporated as if individually set forth.

Although the invention has been described by way of example, and with particular reference to the preferred embodiments shown in the accompanying drawings, it should be appreciated that variations and modifications may be made thereto, without departing from the scope of the invention as defined in the following claims.

I claim:

1. A toothpick holder comprising a peripheral frame defining a space in which a plurality of toothpicks are confined, each toothpick comprising a handle and a blade and formed integrally with but separable from said peripheral frame at an end of the handle remote from the blade, and said peripheral frame providing protection for the one or more toothpicks from forces applied in at least two orthogonal directions.

2. A toothpick holder according to claim 1, further comprising a base plate, said base plate adapted to attach the toothpick holder in a match-book-type folder.

3. A toothpick holder according to claim 2, wherein said base plate is integrally formed with and extends from said peripheral frame and has holes therein for stapling to a match-book-type folder.

4. A toothpick holder according to claim 1, further comprising at least one holding means for retaining a used toothpick.

5. A toothpick holder according to claim 4, wherein said holding means comprises a receiving means on the peripheral frame, said receiving means adapted to receive the handle end of a toothpick removed from the toothpick holder, and retain said removed toothpick securely in the peripheral frame.

6. A toothpick holder according to claim 1, made of plastic material.

7. A toothpick holder according to claim 1, wherein each toothpick blade has a triangular cross-section having an upper edge and angled sides forming a sharpened lower edge, said upper edge forming a point at one end, opposite the handle end, and said sharpened lower edge meeting said point to form a pick end of the toothpick.

8. A toothpick holder according to claim 7, wherein each blade has a substantially scalpel-shape, said sharpened lower edge curving to meet said point of the upper edge to form the pick end.

9. A toothpick holder according to claim 8, wherein the angled sides of the blade form an angle of between substantially 25° and 30° at the sharpened lower edge.

10. A toothpick holder according to claim 1, wherein said handle has a substantially square or rectangular cross-section.

11. A toothpick holder according to claim 1, wherein each adjacent toothpick is oppositely disposed in the peripheral frame.

12. A toothpick holder according to claim 1 wherein each toothpick is connected to the same side of the peripheral frame.

* * * * *

UNITED STATES PATENT AND TRADEMARK OFFICE
CERTIFICATE OF CORRECTION

PATENT NO. : 5,855,215
DATED : January 5, 1999
INVENTOR(S) : Royce Steven CLARKE It is certified that error appears in the above-indentified patent and that said Letters Patent is hereby corrected as shown below:

On the Title Page [54]: Change the title to: TOOTHPICK AND TOOTHPICK HOLDER--.

| Column | Line | |
|---|---|---|
| 1 | 1 | Change "TOOTHPICKS AND TOOTHPICK FRAME" to --TOOTHPICK AND TOOTHPICK HOLDER--. |

Signed and Sealed this

Twenty-sixth Day of October, 1999

*Attest:*

Q. TODD DICKINSON

*Attesting Officer*     *Acting Commissioner of Patents and Trademarks*